US008859826B2

(12) United States Patent
Allgeier et al.

(10) Patent No.: US 8,859,826 B2
(45) Date of Patent: Oct. 14, 2014

(54) PRODUCTION OF ALPHA, OMEGA-DIOLS

(71) Applicant: E I Du Pont De Nemours and Company, Wilmington, DE (US)

(72) Inventors: Alan Martin Allgeier, Wilmington, DE (US); Wathudura Indika Namal De Silva, Wilmington, DE (US); Carl Andrew Menning, Newark, DE (US); Joachim C Ritter, Wilmington, DE (US); Sourav Kumar Sengupta, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/870,080

(22) Filed: Apr. 25, 2013

(65) Prior Publication Data
US 2013/0289312 A1   Oct. 31, 2013

Related U.S. Application Data

(60) Provisional application No. 61/639,449, filed on Apr. 27, 2012.

(51) Int. Cl.
| | |
|---|---|
| *C07C 29/60* | (2006.01) |
| *B01J 23/656* | (2006.01) |
| *B01J 21/06* | (2006.01) |
| *B01J 23/86* | (2006.01) |
| *B01J 29/78* | (2006.01) |
| *B01J 23/89* | (2006.01) |
| *B01J 35/02* | (2006.01) |
| *B01J 29/76* | (2006.01) |
| *B01J 37/00* | (2006.01) |
| *B01J 23/652* | (2006.01) |
| *B01J 37/02* | (2006.01) |
| *C07C 209/16* | (2006.01) |
| *B01J 23/889* | (2006.01) |
| *B01J 29/74* | (2006.01) |

(52) U.S. Cl.
CPC ............. *C07C 29/60* (2013.01); *B01J 23/6567* (2013.01); *B01J 21/063* (2013.01); *B01J 23/868* (2013.01); *B01J 29/78* (2013.01); *B01J 2229/186* (2013.01); *B01J 23/8986* (2013.01); *B01J 35/023* (2013.01); *B01J 29/76* (2013.01); *B01J 23/8993* (2013.01); *B01J 37/0036* (2013.01); *B01J 23/6527* (2013.01); *B01J 37/0201* (2013.01); *C07C 209/16* (2013.01); *B01J 23/8892* (2013.01); *B01J 29/74* (2013.01); *B01J 37/0205* (2013.01)
USPC .......................................... 568/861; 568/903

(58) Field of Classification Search
USPC ........................................................ 568/861
See application file for complete search history.

(56) References Cited

U.S. PATENT DOCUMENTS

| | | | |
|---|---|---|---|
| 2,082,025 A | 6/1937 | Peters | |
| 2,201,347 A | 5/1940 | Rittmeister | |
| 2,440,929 A | 5/1948 | Frederick | |
| 2,768,213 A | 10/1956 | Whetstone et al. | |
| 3,070,633 A | 12/1962 | Utne et al. | |
| 3,083,236 A | 3/1963 | Utne et al. | |
| 3,189,651 A | 6/1965 | Ellery et al. | |
| 3,215,742 A | 11/1965 | Horlenko et al. | |
| 3,223,714 A | 12/1965 | Manly et al. | |
| 3,268,588 A | 8/1966 | Horlenko et al. | |
| 3,270,059 A | 8/1966 | Winderl et al. | |
| 3,917,707 A | 11/1975 | Williams et al. | |
| 3,933,930 A | 1/1976 | Dougherty et al. | |
| 4,254,059 A | 3/1981 | Grey et al. | |
| 4,400,468 A | 8/1983 | Faber | |
| 4,401,823 A | 8/1983 | Arena | |
| 4,780,552 A | 10/1988 | Wambach et al. | |
| 5,112,994 A | 5/1992 | Koseki et al. | |
| 5,210,335 A * | 5/1993 | Schuster et al. | 568/863 |
| 5,412,111 A | 5/1995 | Matsumoto et al. | |
| 5,538,891 A | 7/1996 | Schneider et al. | |
| 5,696,303 A | 12/1997 | Darsow et al. | |
| 5,981,769 A | 11/1999 | Baur et al. | |
| 6,008,418 A | 12/1999 | Baur et al. | |
| 6,087,296 A | 7/2000 | Harper et al. | |
| 6,147,208 A | 11/2000 | Achhammer et al. | |
| 6,265,602 B1 | 7/2001 | Voit et al. | |
| 6,403,845 B1 | 6/2002 | Pfeffinger et al. | |

(Continued)

FOREIGN PATENT DOCUMENTS

| | | |
|---|---|---|
| CA | 2800797 A1 | 12/2011 |
| CN | 101628875 A | 1/2010 |
| CN | 102190639 A | 9/2011 |
| DE | 4238493 C1 | 4/1994 |
| EP | 110089 B1 | 1/1988 |

(Continued)

OTHER PUBLICATIONS

Database CAPLUS on STN, Acc. No. 1979:151575, Nishino et al., JP 53149905 A, Dec. 27, 1978 (abstact).*

(Continued)

*Primary Examiner* — Brian J Davis

(57) ABSTRACT

Disclosed herein are processes for preparing an $\alpha,\omega\text{-}C_n$-diol, wherein n is 5 or greater, from a feedstock comprising a $C_n$ oxygenate. In some embodiments, the process comprises contacting the feedstock with hydrogen gas in the presence of a catalyst comprising metals M1, M2, and M3 and optionally a support, wherein: M1 is Mn, Cr, V, or Ti; M2 is Ni, Co, or Fe; and M3 is Cu, Ag, Pt, Pd or Au; or M1 is Pt or Rh; M2 is Cu, Ni or Pd; and M3 is Mo, Re or W. The $C_n$ oxygenate may be obtained from a biorenewable resource.

7 Claims, No Drawings

(56) References Cited

U.S. PATENT DOCUMENTS

| | | | |
|---|---|---|---|
| 6,407,294 | B1 | 6/2002 | Breitscheidel et al. |
| 6,433,192 | B1 | 8/2002 | Fischer et al. |
| 6,462,220 | B1 | 10/2002 | Luyken et al. |
| 6,593,481 | B1 | 7/2003 | Manzer |
| 6,818,781 | B2 | 11/2004 | Bhatia |
| 7,019,155 | B2 | 3/2006 | Manzer |
| 7,230,145 | B2 | 6/2007 | Kadowaki et al. |
| 8,053,608 | B2 | 11/2011 | Kouno et al. |
| 8,053,615 | B2 | 11/2011 | Cortright et al. |
| 8,501,989 | B2 | 8/2013 | Boussie et al. |
| 8,524,925 | B2 | 9/2013 | Sabesan et al. |
| 8,669,393 | B2 | 3/2014 | Boussie et al. |
| 2003/0212298 | A1 | 11/2003 | Brasse et al. |
| 2006/0014988 | A1 | 1/2006 | Fischer et al. |
| 2007/0287845 | A1 | 12/2007 | Lilga et al. |
| 2008/0200698 | A1 | 8/2008 | Reichert et al. |
| 2009/0156841 | A1 | 6/2009 | Sanborn et al. |
| 2009/0314992 | A1 | 12/2009 | Pinkos et al. |
| 2010/0113841 | A1 | 5/2010 | Suzuki et al. |
| 2010/0216958 | A1 | 8/2010 | Peters et al. |
| 2010/0274030 | A1 | 10/2010 | Bevinakatti et al. |
| 2010/0317822 | A1 | 12/2010 | Boussie et al. |
| 2011/0040131 | A1 | 2/2011 | Kouno et al. |
| 2011/0071306 | A1 | 3/2011 | Robinson |
| 2011/0218318 | A1 | 9/2011 | Boussie et al. |
| 2011/0263916 | A1 | 10/2011 | Bao et al. |
| 2011/0312051 | A1 | 12/2011 | Kalnes et al. |
| 2012/0010419 | A1 | 1/2012 | Pinkos et al. |
| 2012/0022298 | A1 | 1/2012 | Pinkos et al. |
| 2012/0035399 | A1 | 2/2012 | Abillard et al. |
| 2012/0059174 | A1 | 3/2012 | Abillard et al. |
| 2012/0116122 | A1 | 5/2012 | Feist et al. |
| 2012/0172579 | A1 | 7/2012 | Qiao et al. |
| 2013/0172578 | A1 | 7/2013 | Allgeier et al. |
| 2013/0172586 | A1 | 7/2013 | Desilva et al. |
| 2013/0184495 | A1 | 7/2013 | Dias et al. |

FOREIGN PATENT DOCUMENTS

| | | |
|---|---|---|
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A2 | 3/2010 |
| WO | 2010033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

Notice of allowance dated Mar. 11, 2014 for copending U.S. Appl. No. 13/870,091.
Notice of allowance dated Mar. 26, 2014 for copending U.S. Appl. No. 13/870,072.
Co-pending application U.S. Appl. No. 13/870,095, filed Apr. 25, 2013.
Efremov, A.A. et al, "Conversions of Levoglucosenone in Acid Media", Sibirskii Khimicheskii Zhurnal, 1992, 6, 34-39 Translation.
Abe, R. et al, "Photocatalytic overall water splitting under visible light by TaON and WO3 with an IO3-/I-shuttle redox mediator", Chem Commun, 2005, 3829-3831.
Adkins, H. et al, "The catalytic hydrogenation of organic compounds over copper chromite", J Am Chem Soc (1931), vol. 53, 1093.
Alexeev, O.S. et al, "Gamma-Al2O3-Supported Pt catalysts with extremely high dispersions resulting from Pt-W interactions", J Catal, 190 (2000) 157-17.
Binder et al., "Simple chemical transformation of lignocellulosic biomass into furans for fuels and chemicals", J Am Chem Soc (2009) 131, 1979-1985.
Blanc, B. et al, "Starch-derived polyols for polymer technologies: preparation by hydrogenolysis on metal catalysts", Green Chemistry, Apr. 2000, 89-91.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.
Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C—O bond hydrogenolysis of cyclic ethers with OH groups over rhenium-modified supported iridium catalysts", J Catalysis (2012) vol. 294, 171-183.
Chia, M. et al, "Selective hydrogenolysis of polyols and cyclic ethers over bifunctional surface sites on rhodium-rhenium catalysts", J Am Chem Soc (2011) vol. 133, No. 32, 12675-12680.
Connor, R. et al, "Hydrogenolysis of Oxygenated Organic Compounds", J Am Chem Soc (1932), vol. 54, 4678-4690.
Corma, A. "Inorganic Solid Acids and Their Use in Acid-Catalyzed Hydrocarbon Reactions", (1995) Chem. Rev., 95, 559-614.
Diebold, U. "The surface science of titanium dioxide", Surface Science Reports 48 (2003) 53-229.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.
French, G.J. et al, "A re-investigation of the thermal decomposition of ammonium paratungstate", J. Mat. Sci, 16 (1981) 3427-3436.
Gong, L. et al, "Selective hydrogenolysis of glycerol to 1,3-propanediol over a Pt/WO3/TiO2/SiO2 catalyst in aqueous media", Appl Catal A General 390 (2010) 119-126.
Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.
Helberger et al, Justus Liebigs Annalen der Chemie (1949) 561, 215-220.
Huang, L. et al, "Direct conversion of glycerol into 1,3-propanediol over Cu-H4SiW12O40/SiO2 in vapor phase", Catal Lett, 131 (2009) 312-320.
Jae, J. et al, "Investigation into the shape selectivity of zeolite catalysts for biomass conversion", Journal of Catalysis (2011) 279, 257-268.
Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.
Jayaraman, S. et al, "Synthesis and Characterization of Pt-WO3 as Methanol Oxidation Catalysts for Fuel Cells", J Phys Chem B, 2005, 109, 22958-22966.
Jung, M.E. et al, "Synthesis of Methylene-Expanded 2',3'-Dideoxyribonucleosides", J Organic Chemistry 63 (1998) 8133-8144.

(56) References Cited

OTHER PUBLICATIONS

Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.

Karinen, R. et al, "Biorefining: heterogeneously catalyzed reactions of carbohydrates for the production of furfural and hydroxymethyfurfural", Chem Sus Chem (2011) 4, 1002-1016.

Kaufmann, W.E. et al, "The use of platinum oxide as a catalyst in the reduction of organic compounds. IV. Reduction of furfural and its derivatives", J Am Chem Soc (1923) 45, 3029-3044.

Kiss, A.B. et al, "Thermal polycondensation of ammonium paratungstate, $(NH_4)10[W_{12}O_{40}(OH)_2].4H_2O$", J. Materials Sci, 13 (1978) 2541-2547.

Koso, S. et al, "Chemoselective hydrogenolysis of tetrahydrofurfuryl alcohol to 1,5-pentanediol", Chem. Commun. (2009) 2035-2037.

Koso, S. et al, "Promoting effect of Mo on the hydrogenolysis of tetrahydrofurfuryl alcohol to 1,5-pentanediol over $Rh/SiO_2$", J Catalysis 267 (2009), 89-92.

Kuba, S. et al, "Structure and properties of tungstated zirconia catalysts for alkane conversion", J Catalysis, 216 (2003) 353-361.

Lee, U. et al, "Structure of pentasodium trihydrogenhexatungstoplatinate(IV) icosahydrate", Acta Cryst. (1983) C39, 817-819.

Li, N.; Huber, G.W., "Aqueous-phase hydrodeoxygenation of sorbitol with $Pt/SiO_2-Al_2O_3$: identification of reaction intermediates", Journal of Catalysis (2010) 270, 48-59.

Li, N. et al, "Renewable gasoline from aqueous phase hydrodeoxygenation of aqueous sugar solutions prepared by hydrolysis of maple wood", Green Chemistry 2011, 13, 91-101.

Liu, L. et al, "Mesoporous $WO_3$ supported Pt catalyst for hydrogenolysis of glycerol to 1,3-propanediol", Chin. J Catal., 2012, 33, 1257-1261.

Miftakhov, M.S. et al, "Levoglucosenone: the properties, reactions, and use in fine organic synthesis", Russian Chem Reviews (1994) 63(10) 869-882.

Nakagawa, Y. et al, "Heterogeneous catalysis of the glycerol hydrogenolysis", Catal Sci Technol 2011, 1, 179-190.

Nakagawa, Y. et al., "Production of 1,5-pentanediol from biomass via furfural and tetrahydrofurfuryl alcohol", Catalysis Today 195 (2012) 136-143.

Nikolla, E. et al., "'One-Pot' Synthesis of 5-(Hydroxymethyl)furfural from Carbohydrates Using Tin-Beta Zeolite", ACS Catal. (2011), 1, 408-410.

Okuhara, T. et al, "Insoluble heteropoly compounds as highly active catalysts for liquid-phase reactions", J. Mol. Catal. 74 (1992) 247-256.

Ott, L. et al, "Catalytic Dehydration of Glycerol in sub- and supercritical water: a new chemical process for acrolein production", Green Chemistry, 2006, pp. 214-220, vol. 8.

Pae, Y.I. et al, "Characterization of $NiO-TiO_2$ modified with $WO_3$ and catalytic activity for acid catalysis", Bull. Korean Chem. Soc. 2004, vol. 25(12), 1881-1888.

Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.

Roman-Leshkov, Y. et al., "Solvent effects on fructose dehydration to 5-hydroxymethylfurfural in biphasic systems saturated with inorganic salts", Top Catal (2009) 52:297-303.

Shafizadeh, F. et al., "Some Reactions of Levoglucosenone", Carbohydrate Research, 1979, pp. 169-191, vol. 71.

SRI Process Economics Program, 31, Hexamethylenediamine Nov. 1967.

Ten Dam, J. et al, "$Pt/Al_2O_3$ catalyzed 1,3-propanediol formation from glycerol using tungsten additives", ChemCatChem (2013), 5(2), 497-505.

Tong, X. et al, "Biomass into chemicals: conversion of sugars to furan derivatives by catalytic processes", Appl. Catalysis A General, 385 (2010) 1-13.

Tripathy, P.K. et al, "A comparative study on the thermal decomposition of ammonium p-tungstate in batch and fluidized-bed reactors", Ind Eng Chem Res 36 (1997) 3602-3606.

Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.

Xu, W. et al, "Direct catalytic conversion of furfural to 1,5-pentanediol by hydrogenolysis of the furan ring under mild conditions over $Pt/Co_2AlO_4$ catalyst" Chem Comm, Royal Society of Chemistry (2011) vol. 47, No. 13, 3924-3926.

Yamazoe, S. et al, "XAFS Study of Tungsten L1-, L3-Edges: Structural Analysis of Loaded Tungsten Oxide Species", Envir Sci, Research Frontiers 2008, Spring 8, 138-139.

Yamazoe, S. et al, "XAFS Study of Tungsten L1- and L3-Edges: Structural Analysis of $WO_3$ Species Loaded on $TiO_2$ as a Catalyst for Photo-oxidation of $NH_3$", J. Phys Chem C 2008, 112, 6869-6879.

Yoshinaga, Y. et al, "Shape-selective oxidation catalysed by a Pt-promoted ultramicroporous heteropoly compound", J.Chem. Soc. Faraday Trans 1998, 94(15) 2235-2240.

Zanardi, M.M. et al, "Synthesis of a simple chiral auxiliary derived from levoglucosenone and its application in a Diels-Alder reaction", Tetrahedron letters 50 (2009) 999-1002.

Co-pending application, U.S. Appl. No. 14/031,356, filed Sep. 19, 2013.

Co-pending application, U.S. Appl. No. 61/782,172, filed Mar. 14, 2013.

Co-pending application, U.S. Appl. No. 61/782,198, filed Mar. 14, 2013.

Notice of allowance dated Jan. 13, 2014 for copending U.S. Appl. No. 13/729,494.

International Search Report dated Mar. 29, 2013, PCT/US2012/062314.

International Search Report dated Apr. 29, 2013, PCT/US2012/071891.

International Search Report dated Apr. 29, 2013, PCT/US2012/071907.

International Search Report dated Apr. 29, 2013, PCT/US2012/071893.

International Search Report dated Apr. 29, 2013, PCT/US2012/071912.

International Search Report dated Apr. 30, 2013, PCT/US2012/071894.

International Search Report dated Jul. 26, 2013, PCT/US2013/038403.

International Search Report dated Jul. 18, 2013, PCT/US2013/038418.

International Search Report dated Jul. 24, 2013, PCT/US2013/038441.

International Search Report dated Jul. 24, 2013, PCT/US2013/038436.

Office actions dated Jun. 26, 2013 and Sep. 13, 2013 for copending U.S. Appl. No. 13/729,390.

Office actions dated Sep. 27, 2013 and Dec. 17, 2013 for copending U.S. Appl. No. 13/729,464.

Notice of allowance dated Oct. 1, 2013 for copending U.S. Appl. No. 13/729,494.

Notice of allowance dated Nov. 19, 2013 for copending U.S. Appl. No. 13/729,401.

Office action dated Dec. 20, 2013 for copending U.S. Appl. No. 13/729,507.

Office action dated Feb. 27, 2014 for copending U.S. Appl. No. 13/870,095.

Office action dated Feb. 27, 2014 for copending U.S. Appl. No. 13/870,099.

Alamillo, R. et al., "Selective Hydrogenation of Biomass-Derived 5-Hydroxymethylfurfural Using Heterogeneous Catalysts", Green Chem., 2012, 14, 1413.

Jung, K.J. et al., "Furfural Decarbonylation Catalyzed by Charcoal Supported Palladium: Part I—Kinetics", Biomass 16 (1988) 63-76.

Jung, K.J. et al., "Furfural Decarbonylation Catalyzed by Charcoal Supported Palladium: Part II—a Continuous Process", Biomass 16 (1988) 89-96.

(56) References Cited

OTHER PUBLICATIONS

Lichtenthaler, F.W. "Carbohydrates as Organic Raw Materials" 2010 Wiley-VCH Verlag GmbH&Co. KGaA, Weinheim 10.1002/14356007.n05_n07.

Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.

Rao, R.S. et al., "Furfural Hydrogenation Over Carbon-Supported Copper", Catalysis Letters 60 (1999) 51-57.

Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.

International Search Report dated May 6, 2014, PCT/US2012/062314.

Copending application No. PCT/US14/23874 filed Mar. 12, 2014.
Copending application No. PCT/US14/23905 filed Mar. 12, 2014.
Notice of allowance dated Apr. 25, 2014 for copending U.S. Appl. No. 13/729,464.
Notice of allowance dated Apr. 28, 2014 for copending U.S. Appl. No. 13/729,494.
Notice of allowance dated Apr. 29, 2014 for copending U.S. Appl. No. 13/729,507.
Office action dated May 7, 2014 for copending U.S. Appl. No. 13/729,390.
Notice of allowance dated Jun. 10, 2014 for copending U.S. Appl. No. 13/870,091.
Notice of allowance dated Jun. 23, 2014 for copending U.S. Appl. No. 13/870,072.

\* cited by examiner

PRODUCTION OF ALPHA, OMEGA-DIOLS

This application claims priority under 35 U.S.C. §119(e) from, and claims the benefit of U.S. Provisional Application No. 61/639,449 filed Apr. 27, 2012, which is by this reference incorporated in its entirety as a part hereof for all purposes.

FIELD OF DISCLOSURE

The present invention relates to processes for preparing alpha, omega-diols ("α,ω-diols"). More particularly, the present invention relates to processes for preparing α,ω-diols by selective hydrodeoxygenation of oxygenated compounds which can be derived from carbohydrates or biologic sources.

BACKGROUND

Alpha, omega-diols such as 1,5-pentanediol and 1,6-hexanediol are useful as chemical intermediates for the production of, e.g., agrichemicals, pharmaceuticals, and polymers. For example, α,ω-diols can be used as plasticizers and as comonomers in polyesters and polyether-urethanes. It has become increasingly desirable to obtain industrial chemicals such as α,ω-diols, or their precursors, from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon 66. 1,6-Hexanediol can be converted by known methods to 1,6-hexamethylene diamine, a starting component in nylon production. 1,6-Hexanediol is typically prepared from the hydrogenation of adipic acid or its esters or the hydrogenation of caprolactone or its oligomers. For example, in WO 2011/149339, deVries J-G, et al describe a process for the preparation of caprolactone, caprolactam, 2,5-tetrahydrofuran-dimethanol, 1,6-hexanediol or 1,2,6-hexanetriol from 5-hydroxymethyl-2-furfuraldehyde and teach that 1,2,6-hexanetriol may be hydrogenated to 1,6-hexanediol using a catalyst based on palladium, nickel, rhodium, ruthenium, copper and chromium or mixtures thereof. Further, the catalysts may be doped with one or more other elements, such as rhenium.

JP 2003-183200 teaches a method for preparation of 2,5-diethyl-1,6-hexanediol from tetrahydropyran derivatives, e.g. 2,5-diethyltetrahydropyran-2-methanol, comprising hydrogenation of the starting material in the presence of a metal catalyst carried on an acidic support, notably 5% $Pt/Al_2O_3$ and 5% $Pt/SiO_2$—$Al_2O_3$ at 200-240° C. Yields ranged from 40 to 61%.

There is an existing need for processes to make α,ω-diols, especially $C_5$ and $C_6$ α,ω-diols, and synthetic intermediates useful in the production of α,ω-diols, from renewable biosources. There is an existing need for processes to produce 1,5-pentanediol, 1,6-hexanediol, and other α,ω-diols at high yield and high selectivity from biomass-derived starting materials, including 1,2,6-hexanetriol, tetrahydrofuran-2,5-dimethanol, and 2-hydroxymethyltetrahydropyran.

SUMMARY

In one embodiment, a process for preparing an α,ω-$C_n$-diol is provided, the process comprising the steps:
(a) providing a feedstock comprising a $C_n$ oxygenate; and
(b) contacting the feedstock with hydrogen gas, in the presence of a catalyst at a temperature and for a time sufficient to form a product mixture comprising an α,ω-$C_n$-diol, wherein n is 5 or greater; and wherein the catalyst comprises metals M1, M2, and M3 and optionally a support, wherein:
M1 is Mn, Cr, V, or Ti; M2 is Ni, Co, or Fe; and M3 is Cu, Ag, Pt, Pd or Au; or
M1 is Pt or Rh; M2 is Cu, Ni or Pd; and M3 is Mo, Re or W.

In one embodiment, the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In one embodiment, the support comprises $TiO_2$, a zeolite, or mixtures thereof.

In one embodiment, the $C_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural with ketones and/or aldehydes; and condensation products from the reaction of furfural with ketones and/or aldehydes.

In one embodiment, the process further comprises the steps:
(c) optionally, isolating the α,ω-$C_n$-diol from the product mixture;
(d) contacting the α,ω-$C_n$-diol with ammonia and hydrogen in the presence of a reductive amination catalyst at a temperature and for a time sufficient to form a second product mixture comprising an α,ω-$C_n$-diaminoalkane; and
(e) optionally, isolating the α,ω-$C_n$-diaminoalkane from the second product mixture.

DETAILED DESCRIPTION

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "organic compound" means a carbon-containing compound with the following exceptions: binary compounds as the carbon oxides, carbides, carbon disulfide, etc.; ternary compounds such as metallic cyanides, metallic carbonyls, phosgene, carbonylsulfide; and metallic carbonates such as calcium carbonate and sodium carbonate.

As used herein, the term "oxygenate" means an organic compound containing at least one oxygen atom. As used herein, the term "$C_n$ oxygenate" means an oxygenate containing n carbon atoms and, analogously, the term "$C_n$ diol" denotes a diol containing n carbon atoms.

As used herein, the term "biomass" refers to any cellulosic or lignocellulosic material and includes materials comprising hemicellulose, and optionally further comprising lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

As used herein, the term "hemicellulose" means a non-cellulosic polysaccharide found in lignocellulosic biomass. Hemicellulose is a branched heteropolymer consisting of different sugar monomers. It typically comprises from 500 to 3000 sugar monomeric units.

As used herein, the term "lignin" refers to a complex high molecular weight polymer that can comprise guaiacyl units, as in softwood lignin, or a mixture of guaiacyl and syringyl units, as in hardwood lignin.

As uses herein, the term "starch" refers to a carbohydrate consisting of a large number of glucose units joined by glycosidic bonds. Starch, also known as amylum, typically contains amylose and amylopectin.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; examples include xylose, arabinose, lyxose, and ribose. A hexose is a monosaccharide having six carbon atoms; examples include glucose and fructose. Disaccharide molecules consist of two covalently linked monosaccharide units; examples include sucrose, lactose, and maltose. As used herein, "oligosaccharide" molecules consist of about 3 to about 20 covalently linked monosaccharide units. Unless indicated otherwise herein, all references to specific sugars are intended to include the D-stereoisomer, the L-stereoisomer, and mixtures of the stereoisomers.

As used herein, the term "$C_n$ sugar" includes monosaccharides having n carbon atoms; disaccharides comprising monosaccharide units having n carbon atoms; and oligosaccharides comprising monosaccharide units having n carbon atoms. Thus, the term "$C_5$ sugar" includes pentoses, disaccharides comprising pentose units, and oligosaccharides comprising pentose units; the term "$C_6$ sugar" includes hexoses, disaccharides comprising hexose units, and oligosaccharides comprising hexose units.

As used herein, the term "$C_n$ sugar alcohol" refers to compounds produced from $C_n$ sugars by reduction of the carbonyl group to a primary or secondary hydroxyl group. Sugar alcohols having the general formula $H(HCHO)_{x+1}H$, are derived from sugars having the general formula $H(HCHO)_xHCO$. Monosaccharides and disaccharides can be used to form sugar alcohols, though the disaccharides are not fully hydrogenated. Three examples of sugar alcohols are xylitol ($C_5$), sorbitol ($C_6$), and mannitol ($C_6$).

As used herein, the abbreviation "16HD" refers to 1,6-hexanediol. The chemical structure of 1,6-hexanediol is represented by Formula (I).

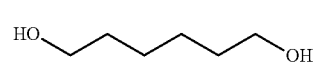

I

As used herein, the abbreviation "15PD" refers to 1,5-pentanediol. The chemical structure of 1,5-pentanediol is represented by Formula (II).

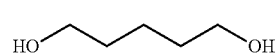

II

As used herein, the abbreviation "126HT" refers to 1,2,6-hexanetriol and includes a racemic mixture of isomers. The chemical structure of 1,2,6-hexanetriol is represented by Formula (III).

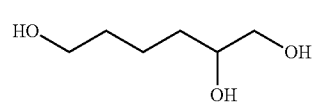

III

As used herein, the abbreviation "125PT" refers to 1,2,5-pentanetriol and includes a racemic mixture of isomers. The chemical structure of 1,2,5-pentanetriol is represented by Formula (IV).

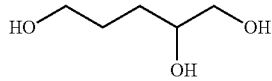

As used herein, the abbreviation "Tetraol" refers to 1,2,5,6-tetrahydroxyhexane, also known as 3,4-dideoxyhexitol, and includes a mixture of stereoisomers. The chemical structure of 1,2,5,6-tetrahydroxyhexane is represented by Formula (V).

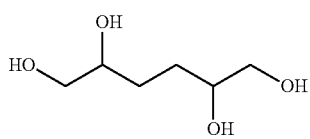

As used herein, the abbreviation "Pentaol" refers to 1,2,3,5,6-hexanepentaol and includes a racemic mixture of isomers. The chemical structure of 1,2,3,5,6-hexanepentaol is represented by Formula (VI).

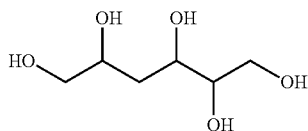

As used herein, the abbreviation "THFdM" refers to tetrahydro-2,5-furandimethanol (also known as tetrahydrofuran-2,5-dimethanol or 2,5-tetrahydrofurandimethanol, or 2,5-bis[hydroxymethyl]tetrahydrofuran) and includes a mixture of stereoisomers (cis and racemic trans isomers). The chemical structure of tetrahydro-2,5-furandimethanol is represented by Formula (VII).

The chemical structure of 2,5-dihydrofuran-2,5-dimethanol is represented by Formula (VIII).

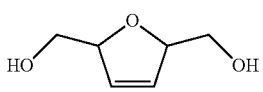

As used herein, the abbreviation "FdM" refers to 2,5-furandimethanol, also known as 2,5-bis(hydroxymethyl)furan. The chemical structure of 2,5-furandimethanol is represented by Formula (IX).

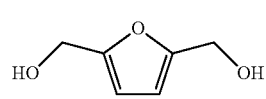

The chemical structure of furfural, also known as furan-2-carbaldehyde or 2-furaldehyde, is represented by Formula (X).

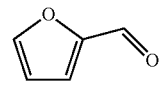

The chemical structure of hydroxymethylfurfural, also known as 5-(hydroxymethyl)-2-furaldehyde, is represented by Formula (XI).

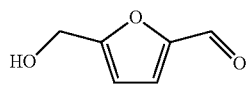

The chemical structure of furfuryl alcohol, also known as 2-furanmethanol, is represented by Formula (XII).

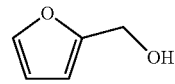

The chemical structure of tetrahydrofurfuryl alcohol, also known as tetrahydro-2-furanmethanol, is represented by Formula (XIII).

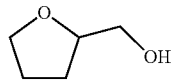

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (XIV).

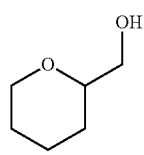

As used herein, the abbreviation "HOTHPM" refers to 2-hydroxymethyl-5-hydroxytetrahydro-2H-pyran, also known as 5-hydroxy-2H-tetrahydropyran-2 methanol or 1,5-anhydro-3,4-dideoxyhexitol, and includes a mixture of stereoisomers. The chemical structure of 2-hydroxymethyl-5-hydroxytetrahydro-2H-pyran is represented by Formula (XV).

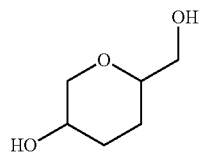

XV

The chemical structure of 3,4-dihydro-2H-pyran-2-carbaldehyde, also known as 3,4-dihydro-2H-pyran-2-carboxaldehyde, 2-formyl-3,4-dihydro-2H-pyran, or "acrolein dimer", is represented by Formula (XVI).

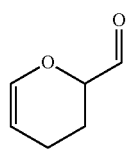

XVI

The chemical structure of levoglucosan, also known as 1,6-anhydro-β-glucopyranose, is represented by Formula (XVII).

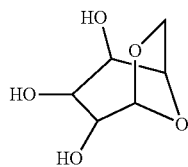

XVII

As used herein, the abbreviations "Lgone" and "LGone" refer to levoglucosenone, also known as 1,6-anhydro-3,4-dideoxy-β-D-pyranosen-2-one. The chemical structure of levoglucosenone is represented by Formula (XVIII).

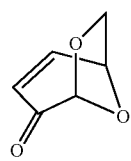

XVIII

The chemical structure of 1,6-anhydro-3,4-dideoxy-p-D-pyranose-2-one is represented by Formula (XIX).

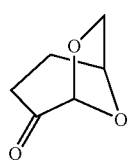

XIX

The chemical structure of levoglucosenol, also known as 1,6-anhydro-3,4-dideoxy-β-erythro-hex-3-enopyranose, is represented by Formula (XX).

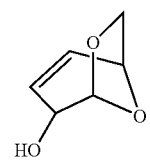

XX

As used herein, the abbreviations "Lgol" and "LGol" refer to levoglucosanol, also known as 1,6-anhydro-3,4-dideoxyhexopyranose, and include a mixture of the threo and erythro stereoisomers. The chemical structure of 1,6-anhydro-3,4-dideoxyhexopyranose is represented by Formula (XXI).

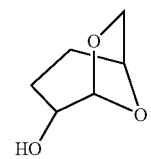

XXI

As used herein, the abbreviation "ISOS" refers to isosorbide, also known as 1,4:3,6-dianhydrosorbitol or 1,4-dianhydrosorbitol. The chemical structure of isosorbide is represented by Formula (XXII).

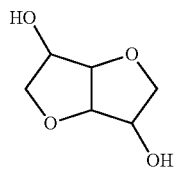

XXII

The chemical structure of sorbitol, also known as hexane-1,2,3,4,5,6-hexol, is represented by Formula (XXIII).

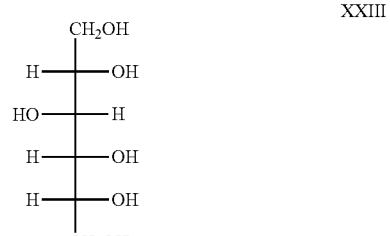

XXIII

The chemical structure of glucose, also known as dextrose or 2,3,4,5,6-pentahydroxyhexanal, is represented by Formula (XXIV).

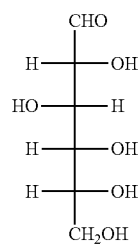

XXIV

The chemical structure of fructose, also known as levulose, is represented by Formula (XXV).

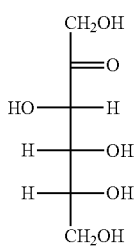

The chemical structure of xylitol, also known as pentane-1,2,3,4,5-pentol, is represented by Formula (XXVI).

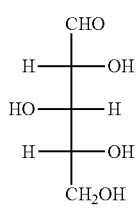

In one embodiment, a process is provided for preparing an α,ω-$C_n$-diol, the process comprising the steps:

(a) providing a feedstock comprising a $C_n$ oxygenate; and (b) contacting the feedstock with hydrogen gas, in the presence of a catalyst at a temperature and for a time sufficient to form a product mixture comprising an α,ω-$C_n$-diol, wherein n is 5 or greater; and wherein the catalyst comprises metals M1, M2, and M3, and optionally a support, wherein M1 is Mn, Cr, V, or Ti; M2 is Ni, Co, or Fe; and M3 is Cu, Ag, Pt, Pd or Au; or M1 is Pt or Rh; M2 is Cu, Ni or Pd; and M3 is Mo, Re or W.

In one embodiment, n=5 or 6. In one embodiment, n=5, and the α,ω-$C_n$-diol is 1,5-pentanediol. In one embodiment, n=6, and the α,ω-$C_n$-diol is 1,6-hexanediol. In one embodiment, n=7, and the α,ω-$C_n$-diol is 1,7-heptanediol. In one embodiment, n=8, and the α,ω-$C_n$-diol is 1,8-octanediol.

In one embodiment, the catalyst comprises metals M1, M2, and M3 and optionally a support; wherein M1 is Mn, Cr, V, or Ti; M2 is Ni, Co, or Fe; and M3 is Cu, Ag, Pt, Pd or Au. In one embodiment, the catalyst comprises metals M1, M2, and M3 and optionally a support; wherein M1 is Mn or Cr; M2 is Ni, Co, or Fe; and M3 is Cu.

In one embodiment, the catalyst comprises metals M1, M2, and M3 and optionally a support; wherein M1 is Pt or Rh; M2 is Cu, Ni or Pd; and M3 is Mo, Re or W. In one embodiment, the catalyst comprises metals M1, M2, and M3 and optionally a support; wherein M1 is Pt or Rh; M2 is Cu or Ni; and M3 is Re or W.

Examples of $C_n$ oxygenates that are suitable for use in the present processes include 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxy-hexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes. The feedstock may comprise one or more Cn oxygenates.

In one embodiment, the $C_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof. These $C_n$ oxygenates are useful for preparation of reaction mixtures comprising 1,6-hexanediol by the processes disclosed herein. In one embodiment, the $C_n$ oxygenate comprises 1,2,6-hexanetriol.

In one embodiment, the $C_n$ oxygenate comprises 1,2,5-pentanetriol; furfural; furfuryl alcohol; tetrahydrofurfuryl alcohol; xylitol; or mixtures thereof. These $C_n$ oxygenates are useful for preparation of product mixtures comprising 1,5-hexanediol by the processes disclosed herein.

Examples of suitable pentoses include without limitation xylose, arabinose, lyxose, xylitol, and ribose. Examples of suitable hexoses include without limitation glucose, mannose, fructose, and galactose. Examples of condensation products from the reaction of furfural or 5-(hydroxymethyl)-2-furfural with ketones and/or aldehydes are described in Synthesis (2008), (7), 1023-1028 (e.g., CAS Reg. No. 1040375-91-4 and CAS Reg. No. 886-77-1) ; and in ChemSusChem (2010), 3(10), 1158-1161, in which subjecting furfural and 5-(hydroxymethyl)-2-furfural to aldol condensation produced molecules having 8 to 15 carbon atoms.

Suitable $C_n$ oxygenates can be derived from biorenewable resources including biomass. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment, the $C_n$ oxygenate is ultimately derived from corn cobs, sugar cane bagasse, switchgrass, wheat straw, sawdust and other wood waste, and lignocellulosic feedstocks.

A biorenewable resource such as biomass can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research*, 71, 169-191 (1979)).

Glycerol can be obtained from a biorenewable resource, for example from hydrolysis of vegetable and animal fats and oils (that is, triacylglycerides comprising ester functionality resulting from the combination of glycerol with $C_{12}$ or greater fatty acids). 1,2,6-Hexanetriol can be obtained from materials such as glucose, cellulose or glycerol derived from a biorenewable resource. For example, 1,2,6-hexanetriol can be obtained by a process comprising the steps of contacting glycerol with a catalyst to prepare acrolein, heating acrolein (optionally in the presence of a catalyst) to prepare 2-formyl-3,4-dihydro-2H-pyran, contacting 2-formyl-3,4-dihydro-2H-pyran with water to prepare 2-hydroxyadipic aldehyde and contacting 2-hydroxyadipic aldehyde with hydrogen and a catalyst to produce a product mixture comprising 1,2,6-hexanetriol. See, for example, U.S. Pat. No. 2,768,213, German Patent No. 4238493, and L. Ott, et al. in *Green Chem.*, 2006, 8, 214-220.

The catalysts utilized in the process described herein can be synthesized by any conventional method for preparing catalysts, for example, deposition of metal salts from aqueous or organic solvent solutions via impregnation or incipient wetness, precipitation of an M1 component and/or an M2 component and/or an M3 component, or solid state synthesis. Preparation may comprise drying catalyst materials under elevated temperatures from 30-250° C., preferably 50-150° C.; calcination by heating in the presence of air at temperatures from 250-800° C., preferably 300-450° C.; and reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

The loading of M1 may be 0.1-50% but preferably 0.5-5% by weight, based on the weight of the prepared catalyst (i.e., including the catalyst support where present). The loading of M2 may be 0.1-99.9%, for example 2-10%, or 0.5-5%. The loading of M3 may be 0.1-99%, for example 2-10%. Preferably the molar ratio of M1 to M2 to M3 in the catalysts is in the range of 0.1-1.0:0.1-1.0:1.0. Regarding the M1, M2, and M3 loadings, all percentages are intended as weight percent relative to the total weight of the prepared catalyst. In some embodiments, the molar ratio of M1, M2, and M3 in the catalyst is such that M3/(M1+M2) is from about 1.1:1 to about 1:1.1, for example about 1:1.

In some embodiments, it is useful to utilize a catalyst which comprises a solid support to enhance the stability and economic feasibility of the process. Examples of useful supports include $WO_3$, $SiO_2$, $Al_2O_3$, carbon, SiC, $TiO_2$, $ZrO_2$, $SiO_2$—$Al_2O_3$, clays such as montmorillonite, $SiO_2$—$TiO_2$, tungstated $ZrO_2$, $V_2O_5$, $MoO_3$, and zeolites such as H-Y, FAU (H-Y or USY), BEA (H-Beta), MFI (H-ZSM5), MEL (H-ZSM11) and MOR (H-Mordenite). Typically, tungstated $ZrO_2$ can comprise up to about 19 wt % W as $WO_3$ on $ZrO_2$, see for example S. Kuba et al in Journal of Catalysis 216 (2003), p. 353-361. In one embodiment, the catalyst further comprises a solid support comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$,H—Y zeolites, $V_2O_5$, $MoO_3$, or mixtures thereof. In one embodiment, the support comprises $TiO_2$, a zeolite, or mixtures thereof. In other embodiments, it may be desirable to not have a support.

The prepared catalyst can be in any physical form typical for heterogeneous catalysts, including but not limited to powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above. When a solid support is utilized, it is desirable that M1 be intimately associated with the M2 component, the M3 component, or both, as measured by transmission electron microscopy with energy dispersive spectroscopy. It is further preferable that the particle size of the M1 component be less than 10 nm and most preferably less than 3 nm as measured by the same techniques. In this case, particle size of the M1 component may refer to that of a mixture of the M1 and M2 components, an alloy of the M1 and M2 components, a particle of the M1 component adjacent to a particle of the M2 component, or a particle of the M1 component on the support which contains the M2 component.

The catalyst may be present in any weight ratio to the feedstock sufficient to catalyze the selective hydrodeoxygenation, generally in the range of 0.0001:1 to 1:1, preferably 0.001:1 to 0.5:1 for batch reactions. For continuous reactions, the same ratios are appropriate where the weight ratio of feed to catalyst is defined as weight of $C_n$ oxygenate feed processed per weight of catalyst.

Useful temperatures for the processes are between about 30° C. and about 300° C. In some embodiments, the temperature is between and optionally includes any two of the following values: 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., and 300° C. It is expected that with some catalysts, temperatures above about 300° C. could be used.

The process is conducted by contacting a Cn oxygenate feed with hydrogen in the presence of the catalyst for a time sufficient to form a product mixture comprising an $\alpha,\omega$-$C_n$-diol. The mole ratio of hydrogen to feed is not critical as long as sufficient hydrogen is present to produce the desired $\alpha,\omega$-$C_n$-diol. Hydrogen is preferably used in excess, and may optionally be used in combination with an inert gas such as nitrogen or argon. If an inert gas is used in combination with the hydrogen, the amount of the inert gas should be such that it does not negatively impact the formation of the product mixture. The pressure of the process may be between about 300 kPa and about 25,000 kPa. In some embodiments, the pressure of the process is between and optionally includes any two of the following values: 300; 500; 1000; 1500; 2000; 2500; 3000; 3500; 4000; 4500; 5000; 10,000; 15,000; 20,000; and 25,000 kPa.

The process is typically conducted in the presence of a solvent, which may serve to reduce the viscosity of the system to improve fluidity of the catalyst in the reaction vessel and/or to remove the heat of reaction and improve the performance of the process. Polar solvents are preferred. The solvent may be present in a range of 1% to 95% by weight of the total reaction mixture, excluding the catalyst.

The reaction products may be isolated or purified by any common methods known in the art including but not limited to distillation, wiped film evaporation, chromatography, adsorption, crystallization, and membrane separation.

It will be appreciated that the processes disclosed herein can also be utilized to prepare useful intermediates or byproducts in the synthesis of the $\alpha,\omega$-diols through optimization of the process parameters. Examples of intermediates that can be prepared during synthesis of 1,5-pentanediol and/or 1,6-hexanediol include but are not limited to furan dimethanol: tetrahydrofuran dimethanol; tetrahydropyran-2-methanol; levoglucosanol; and furfuryl alcohol. Examples of byproducts which can be obtained during synthesis of 1,5-pentanediol and/or 1,6-hexanediol include but are not limited to isomeric hexanols; isomeric pentanols; 1,5-hexanediol; 1,2-hexanediol; 2-methyltetrahydropyran; 2,5-dimethyltetrahydrofuran; 1,2-cyclohexanediol; 1,2-cyclopentanediol; cyclohexanol, and mixtures thereof.

The α,ω-C$_n$-diols obtained by the processes disclosed herein can be converted to industrially useful materials such as α,ω-C$_n$-diaminoalkanes. For example, 1,5-pentanediol and 1,6-hexanediol can be reductively aminated to 1,5-pentanediamine (1,5-diaminopentane) and 1,6-hexanediamine (1,6-diaminohexane), respectively, by methods known in the art. See, for example, U.S. Pat. Nos. 3,215,742; 3,268,588; and 3,270,059.

In some embodiments, the processes disclosed herein further comprise the steps:

(c) optionally, isolating the α,ω-C$_n$-diol from the product mixture;

(d) contacting the α,ω-C$_n$-diol with ammonia and hydrogen in the presence of a reductive amination catalyst at a temperature and for a time sufficient to form a second product mixture comprising an α,ω-C$_n$-diaminoalkane; and (e) optionally, isolating the α,ω-C$_n$-diaminoalkane from the second product mixture.

In one embodiment, the α,ω-C$_n$-diaminoalkane comprises 1,6-diaminohexane. In one embodiment, the α,ω-C$_n$-diaminoalkane comprises 1,5-diaminopentane.

The reductive amination catalyst contains at least one element selected from Groups IB, VIB, VIIB, and VIII of the Periodic Table, for example iron, cobalt, nickel, ruthenium, rhodium, palladium, osmium, copper, chromium, iridium, or platinum. The elements may be in the zero oxidation state or in the form of a chemical compound. The reductive amination catalyst may be supported, unsupported or Raney-type. In one embodiment, the reductive amination catalyst contains ruthenium. In one embodiment, the reductive amination catalyst contains nickel. In one embodiment, the reductive amination catalyst is Raney nickel. In one embodiment, the reductive amination catalyst is Raney copper. In one embodiment, the reductive amination catalyst is Raney cobalt.

The reductive amination step is conducted by contacting the α,ω-C$_n$-diol, or a product mixture comprising the α,ω-C$_n$-diol, with ammonia and hydrogen in the presence of the catalyst for a time sufficient to form a second product mixture comprising an α,ω-C$_n$-diaminoalkane. Useful temperatures for the reductive amination step are in the range of about 40° C. to 300° C., for example in the range of about 75° C. to 150° C. Typically pressures are in the range of about 2 MPa to 35 MPa, for example in the range of about 4 MPa to 12 MPa. The molar ratio of hydrogen to the α,ω-C$_n$-diol is typically equal to or greater than 1:1, for example in the range of 1:1 to 100:1, or in the range of 1:1 to 50:1.

The reductive amination step is typically performed in liquid ammonia solvent. The ammonia is used in stoichiometric excess with reference to the α,ω-C$_n$-diol. Typically, a molar ratio of 1:1 to 80:1 of ammonia to the α,ω-C$_n$-diol can be used, for example a molar ratio in the range of 10:1 to 50:1. Optionally, an additional solvent such as water, methanol, ethanol, butanol, pentanol, hexanol, an, ester, a hydrocarbon, tetrahydrofuran, or dioxane, can be used. The weight ratio of the additional solvent to the α,ω-C$_n$-diol is typically in the range of 0.1:1 to 5:1.

The reductive amination step can be performed in a fixed bed reactor or in a slurry reactor, for example a batch, continuous stirred tank reactor or bubble column reactor. The α,ω-C$_n$-diamine may be isolated from the second product mixture by any common methods known in the art, for example fractional distillation under moderate vacuum.

EXAMPLES

The processes described herein are illustrated in the following examples. From the above discussion and these examples, one skilled in the art can ascertain the essential characteristics of this invention, and without departing from the spirit and scope thereof, can make various changes and modifications to adapt it to various uses and conditions.

The following abbreviations are used in the examples: "° C." means degrees Celsius; "wt %" means weight percent; "g" means gram; "mg" means milligrams; "m$^2$/g" means square meters per gram; "psi" means pounds per square inch; "mL" means milliliter; "kPa" means kilopascal; "MPa" means megapascal; "GC" means gas chromatography; "Temp" means temperature; "Ex" means Example, "cony" means conversion; "sel" means selectivity.

Materials

All commercial materials were used as received unless stated otherwise. 1,2,6-Hexanetriol (>=97 GC area % purity) was obtained from Evonik DEGUSSA GmBH, Marl, Germany.

The following metal salts were used in the catalyst syntheses described herein.

| Metal Salt | Source |
| --- | --- |
| Rhodium (III) Chloride Hydrate | Strem |
| Tetraammineplatinum (II) Nitrate | Aldrich |
| Copper (II) Nitrate Hydrate | Alfa Aesar |
| Palladium Nitrate | Alfa Aesar |
| Nickel (II) Chloride Hexahydrate | Aldrich |
| Nickel (II) Nitrate Hexahydrate | Aldrich |
| Ammonium Perhenate | Aldrich |
| Ammonium Tungsten Oxide Hydrate | Alfa Aesar |
| Manganese (II) Nitrate Hydrate | Alfa Aesar |
| Cobalt (II) Nitrate Hexahydrate | Aldrich |
| Iron (III) Nitrate Nonahydrate | Aldrich |
| Chromium (III) Nitrate Nonahydrate | Aldrich |

Nickel(II) chloride hexahydrate was used as the Ni salt for the Ni-containing catalysts listed in Tables 1 and 2. Nickel(II) nitrate hexahydrate was used as the Ni salt for the Ni-containing catalysts listed in Table 3.

Titanium dioxide (Aerolyst 7711) was obtained from Evonik. Zeolite Y (CBV 780) having a SiO$_2$ to Al$_2$O$_3$ molar ratio of 80:1, a nominal cation form of hydrogen, a Na$_2$O content of 0.03 wt %, unit cell size A=24.24, and a surface area of 780 m$^2$/g was obtained from Zeolyst.

Percent conversion of 126HT and percent selectivity to 16HD are defined as follows:

$$\% \text{ Conversion} = \frac{100 * (\text{mol starting material charged} - \text{mol starting material remaining})}{\text{mol starting material charged}}$$

$$\% \text{ Selectivity} = \frac{100 * \text{mol of product compound}}{(\text{mol starting material charged} - \text{mol starting material remaining})}$$

Synthesis of Pt/Cu/W/TiO$_2$ Catalyst

A Pt/Cu/W/TiO$_2$ catalyst containing 1.8 wt % Pt, 1.8 wt % Cu, and 6.9 wt % W supported on TiO$_2$ was synthesized using the following procedure. Titanium dioxide (0.8842 g), which had been ground and passed through a 400 micron mesh sieve and wetted with 1.0 mL of water, was impregnated with 0.0396 g of tetraammineplatinum (II) nitrate in 1.0 mL of water. The slurry was vortexed for 15 minutes and then dried overnight under vacuum at 110° C. The resulting solid was allowed to cool to room temperature and wetted again with 1.0 mL of water, and impregnated with a solution of Cu (NO$_3$)$_2$3H$_2$O (0.076 g) in 1.0 mL of water. The slurry was vortexed for 15 minutes and then dried overnight under vacuum at 110° C. The resulting solid was allowed to cool to room temperature and wetted again with 1.0 mL of water, and impregnated with a solution of ammonium tungsten oxide hydrate (0.1089 g) in 3.0 mL of water. Once again, the slurry was vortexed for 15 minutes and then dried overnight under vacuum at 110° C. The resulting material was transferred to a ceramic boat and calcined in air at 400° C. for three hours.

Additional M1/M2/M3/support catalysts were prepared using the procedure described above and the metal salts and catalyst supports described in the Materials section. The catalysts and their weight percentages of M1, M2, and M3 are given in Tables 1, 2, and 3.

Examples 1-29

The M1/M2/M3/support catalysts prepared as described above were evaluated for the hydrodeoxygenation of 1,2,6-hexanetriol to 1,6-hexanediol according to the following procedure.

In each of Examples 1-29, the conversion of 1,2,6-hexanetriol to a reaction mixture comprising 1,6-hexanediol was performed by placing approximately 1 g of an aqueous solution of 126HT (5 wt %) and approximately 50 mg of the prepared catalyst as indicated in Table 1, 2, or 3 with a stir bar into a 1.5 mL pressure vessel. The vessel was charged with $H_2$ to a pre-reduction pressure of 145 psi (1000 kPa). The reactor was then heated to the reaction temperature shown in Table 1, 2, or 3. The vessel contents were stirred for 1 hour and then the pressure was increased to 900-1000 psi (6200-6900 kPa); the reaction pressure and temperature were maintained for 4 hours. The vessel was then cooled to room temperature. The reaction mixture was filtered and the product solution analyzed using GC methods. Typically, product solutions contained 1,5-pentanediol, 1,2-hexanediol, and/or 2-hydroxymethyltetrahydropyran in addition to 1,6-hexanediol.

Results for M1/M2/M3/support catalysts wherein M1 was Pt are presented in Table 1. Results for M1/M2/M3/support catalysts wherein M1 was Rh are presented in Table 2. Results for M1/M2/M3/support catalysts wherein M1 was Mn or Cr are presented in Table 3.

In the Tables, the M1, M2, and M3 components of the catalyst compositions are referred to as "M1 (x %)", "M2 (y %)", "M3 (z %)" wherein x, y, and z mean the weight percentages of metals M1, M2 and M3 respectively, based on the total weight of the prepared catalyst. For Examples 1-23, conversion and selectivity results were calculated using uncalibrated GC peak area percentages. For Examples 24-29, conversion and selectivity results were calculated using calibrated GC peak area percentages.

TABLE 1

Conversion (Conv) of 1,2,6-Hexanetriol (126HT) and Selectivity (Sel) to 1,6-Hexanediol (16HD) with M1/M2/M3 Catalysts Supported on $TiO_2$ wherein M1 is Pt; M2 is Cu, Ni, or Pd; and M3 is Re or W.

| Ex | Temp (° C.) | M1 (wt %) | M2 (wt %) | M3 (wt %) | M1:M2:M3 Molar Ratio | Conv (%) | Sel to 16HD (%) |
|---|---|---|---|---|---|---|---|
| 1 | 180 | Pt (1.8) | Cu (1.8) | Re (6.9) | 0.09:2.8:3.7 | 15.2 | 45.1 |
| 2 | 180 | Pt (1.8) | Cu (1.8) | W (6.9) | 0.09:2.8:3.7 | 5.9 | 35.9 |
| 3 | 180 | Pt (1.8) | Ni (1.8) | Re (7.3) | 0.09:3.0:3.9 | 38.6 | 38.0 |
| 4 | 180 | Pt (1.8) | Ni (1.8) | W (7.3) | 0.09:3.0:3.9 | 3.7 | 22.3 |
| 5 | 180 | Pt (1.8) | Pd (1.8) | W (5.0) | 0.09:1.7:2.7 | 60.1 | 50.5 |

TABLE 2

Conversion (Conv) of 1,2,6-Hexanetriol (126HT) and Selectivity (Sel) to 1,6-Hexanediol (16HD) with M1/M2/M3 Catalysts Supported on $TiO_2$ or Zeolite CBV780, Wherein M1 is Rh; M2 is Cu, Ni, or Pd; and M3 is Re or W.

| Ex | Temp (° C.) | M1 (wt %) | M2 (wt %) | M3 (wt %) | M1:M2:M3 Molar Ratio | Support | Conv (%) | Sel to 16HD (%) |
|---|---|---|---|---|---|---|---|---|
| 6 | 120 | Rh(1.8) | Cu(1.8) | Re(8.3) | 1.7:2.8:4.5 | zeolite | 7.6 | 57.4 |
| 7 | 120 | Rh(1.8) | Cu(1.8) | W(8.3) | 1.7:2.8:4.5 | zeolite | 1.1 | 10.3 |
| 8 | 120 | Rh(1.8) | Cu(1.8) | Re(8.3) | 1.7:2.8:4.5 | $TiO_2$ | 7.8 | 46.0 |
| 9 | 120 | Rh(1.8) | Cu(1.8) | W(8.3) | 1.7:2.8:4.5 | $TiO_2$ | 2.5 | 37.8 |
| 10 | 160 | Rh(1.8) | Cu(1.8) | Re(8.3) | 1.7:2.8:4.5 | $TiO_2$ | 27.7 | 31.4 |
| 11 | 160 | Rh(1.8) | Cu(1.8) | W(8.3) | 1.7:2.8:4.5 | $TiO_2$ | 11.4 | 32.1 |
| 12 | 120 | Rh(1.8) | Ni(1.8) | Re(8.7) | 1.7:3:1:4.7 | zeolite | 9.0 | 52.2 |
| 13 | 120 | Rh(1.8) | Ni(1.8) | W(8.6) | 1.7:3:1:4.7 | zeolite | 1.6 | 9.9 |
| 14 | 120 | Rh(1.8) | Ni(1.8) | Re(8.7) | 1.7:3:1:4.7 | $TiO_2$ | 5.8 | 31.0 |
| 15 | 120 | Rh(1.8) | Ni(1.8) | W(8.6) | 1.7:3:1:4.7 | $TiO_2$ | 5.0 | 3.2 |
| 16 | 160 | Rh(1.8) | Ni(1.8) | Re(8.7) | 1.7:3:1:4.7 | $TiO_2$ | 42.6 | 23.4 |
| 17 | 160 | Rh(1.8) | Ni(1.8) | W(8.6) | 1.7:3:1:4.7 | $TiO_2$ | 2.8 | 18.5 |
| 18 | 120 | Rh(1.8) | Pd(1.8) | W(6.4) | 1.7:1.7:3.4 | zeolite | 4.5 | 38.2 |
| 19 | 120 | Rh(1.8) | Pd(1.8) | Re(6.4) | 1.7:1.7:3.4 | zeolite | 28.2 | 66.4 |
| 20 | 120 | Rh(1.8) | Pd(1.8) | W(6.4) | 1.7:1.7:3.4 | $TiO_2$ | 1.9 | 28.9 |
| 21 | 120 | Rh(1.8) | Pd(1.8) | Re(6.4) | 1.7:1.7:3.4 | $TiO_2$ | 34.6 | 56.2 |
| 22 | 160 | Rh(1.8) | Pd(1.8) | W(6.4) | 1.7:1.7:3.4 | $TiO_2$ | 23.1 | 30.4 |
| 23 | 160 | Rh(1.8) | Pd(1.8) | Re(6.4) | 1.7:1.7:3.4 | $TiO_2$ | 72.4 | 23.7 |

TABLE 3

Conversion (Conv) of 1,2,6-Hexanetriol (126HT) and Selectivity (Sel) to 1,6-Hexanediol (16HD) with M1/M2/M3 Catalysts Supported on $TiO_2$ Wherein M1 is Mn or Cr; M2 is Ni, Co, or Fe; and M3 is Cu.

| Ex | Temp (° C.) | M1 (wt %) | M2 (wt %) | M3 (wt %) | M1:M2:M3 Molar Ratio | Conv (%) | Sel to 16HD (%) |
|---|---|---|---|---|---|---|---|
| 24 | 260 | Mn (1.3) | Ni (0.6) | Cu (4.4) | 0.02:0.01:0.07 | 53 | 12 |
| 25 | 260 | Cr (0.4) | Ni (1.6) | Cu (4.4) | 0.02:0.01:0.07 | 41 | 17 |
| 26 | 260 | Mn (1.1) | Co (0.8) | Cu (4.4) | 0.02:0.01:0.07 | 44 | 13 |
| 27 | 260 | Cr (0.4) | Co (1.6) | Cu (4.4) | 0.02:0.01:0.07 | 37 | 17 |

TABLE 3-continued

Conversion (Conv) of 1,2,6-Hexanetriol (126HT) and Selectivity (Sel) to 1,6-Hexanediol (16HD) with M1/M2/M3 Catalysts Supported on $TiO_2$ Wherein M1 is Mn or Cr; M2 is Ni, Co, or Fe; and M3 is Cu.

| Ex | Temp (° C.) | M1 (wt %) | M2 (wt %) | M3 (wt %) | M1:M2:M3 Molar Ratio | Conv (%) | Sel to 16HD (%) |
|---|---|---|---|---|---|---|---|
| 28 | 260 | Mn (0.9) | Fe (1.0) | Cu (4.4) | 0.02:0.18:0.07 | 39 | 12 |
| 29 | 260 | Cr (0.9) | Fe (1.0) | Cu (4.4) | 0.02:0.18:0.07 | 31 | 11 |

What is claimed is:

1. A process for preparing an $\alpha,\omega$-$C_n$-diol, comprising the steps:
(a) providing a feedstock comprising a $C_n$ oxygenate comprising 1,2,6-hexanetriol; and
(b) contacting the feedstock with hydrogen gas, in the presence of a catalyst at a temperature and for a time sufficient to form a product mixture comprising an $\alpha,\omega$-$C_n$-diol, wherein n is 6;
and wherein the catalyst comprises metals M1, M2, and M3, and optionally a support, wherein
M1 is Mn or Cr; M2 is Ni, Co, or Fe; and M3 is Cu; or
M1 is Pt or Rh; M2 is Cu, Ni or Pd; and M3 is Re or W.

2. The process of claim 1, wherein the optional support is present in the catalyst and comprises $WO_3$, $SiO_2$, $Al_2O_3$, carbon, $TiO_2$, $ZrO_2$, $SiO_2$-$Al_2O_3$, montmorillonite, $SiO_2$-$TiO_2$, tungstated $ZrO_2$, zeolites, $V_2O_5$, $MoO_3$, or mixtures thereof.

3. The process of claim 1, wherein M1 is Mn or Cr; M2 is Ni, Co, or Fe; and M3 is Cu.

4. The process of claim 1, wherein M1 is Pt or Rh; M2 is Cu, Ni or Pd; and M3 is Re or W.

5. The process of claim 4, wherein M1 is Pt or Rh; M2 is Cu or Ni; and M3 is Re or W.

6. The process of claim 2, wherein the support comprises $TiO_2$, a zeolite, or mixtures thereof.

7. The process of claim 1, further comprising the steps:
(c) optionally, isolating the $\alpha,\omega$-$C_n$-diol from the product mixture;
(d) contacting the $\alpha,\omega$-$C_n$-diol with ammonia and hydrogen in the presence of a reductive amination catalyst at a temperature and for a time sufficient to form a second product mixture comprising an $\alpha,\omega$-$C_n$-diaminoalkane, wherein the $\alpha,\omega$-$C_n$-diaminoalkane comprises 1,6-diaminohexane; and
(e) optionally, isolating the $\alpha,\omega$-$C_n$-diaminoalkane from the second product mixture.

* * * * *